United States Patent [19]
Henderson et al.

[11] Patent Number: 5,583,253
[45] Date of Patent: Dec. 10, 1996

[54] METHOD OF PREPARING PURIFIED ALKANESULFONIC ACID

[76] Inventors: Phyllis A. Henderson, 1254 Lindbergh St., Wyandotte, Mich. 48192; Steven G. Schon, 454 Saunders Dr., Strafford, Pa. 19087; Carl Postuma, 2242 Draper St., Ypsilanti, Mich. 48197

[21] Appl. No.: 676,143

[22] Filed: Mar. 27, 1991

[51] Int. Cl.$^6$ ........................................ C07C 61/00
[52] U.S. Cl. .................... 562/124; 562/118; 562/119; 562/115
[58] Field of Search ................... 562/124, 118, 562/119, 115

[56] References Cited

U.S. PATENT DOCUMENTS

| | | |
|---|---|---|
| 3,626,004 | 12/1971 | Guertin . |
| 4,450,047 | 5/1984 | Malzahn . |
| 4,699,736 | 10/1987 | Gongora et al. . |
| 4,859,373 | 8/1989 | Olliver et al. ........................ 562/119 |
| 4,895,977 | 1/1990 | Nosowitz ............................. 562/118 |
| 4,938,846 | 7/1990 | Comstock et al. . |

FOREIGN PATENT DOCUMENTS

| | | |
|---|---|---|
| 0373305 | 6/1990 | European Pat. Off. . |
| 1350328 | 4/1974 | United Kingdom . |
| 1350328 | 4/1978 | United Kingdom . |

OTHER PUBLICATIONS

Chemical Abstracts, vol. 79, No. 3, 23 Jul. 1973, Columbus, Ohio, U.S.A., Abstract No. 18083 v, p. 402 1990 R. Oda et al. "Methanesulfonic Acid".

Chemical Abstracts, vol. 79, p. 402—item 18083v., Jul. 1973 (Abstract of Japan Kokai 73 22423).

*Primary Examiner*—Marianne M. Cintins
*Assistant Examiner*—Keith MacMillan

[57] ABSTRACT

A process of preparing purified alkanesulfonic acid from crude aqueous alkanesulfonic acid containing oxidizable impurities wherein the crude material is treated with a sufficient amount of chlorine to convert the oxidizable impurities to alkanesulfonyl chloride and then hydrolyzing said alkanesulfonyl chloride to alkanesulfonic acid by heating.

12 Claims, 1 Drawing Sheet

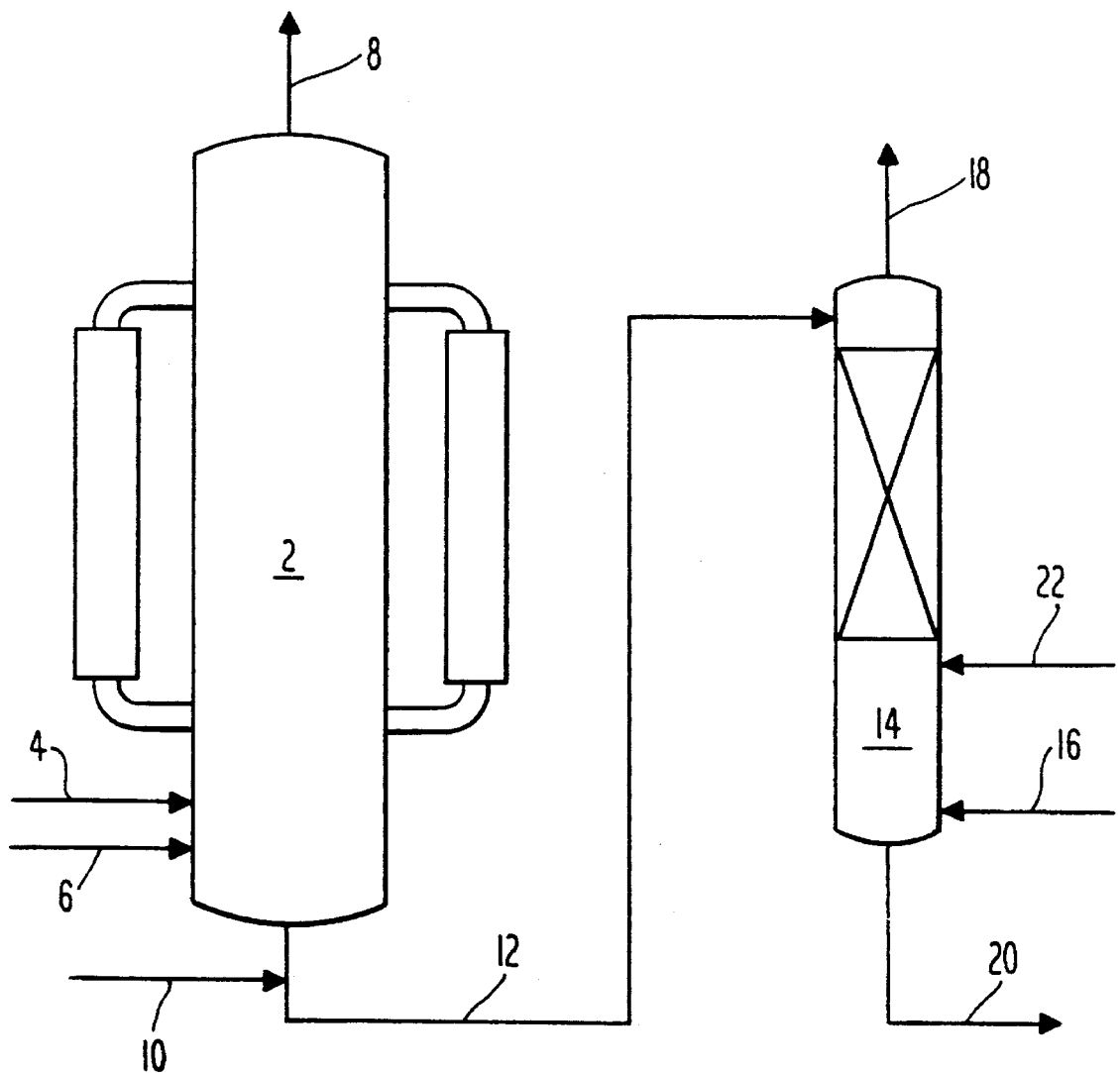
_Fig. 1_

METHOD OF PREPARING PURIFIED ALKANESULFONIC ACID

BACKGROUND OF THE INVENTION

This invention concerns the purification of crude aqueous alkanesulfonic acid containing oxidizable impurities. More particularly, it relates to the use of chlorine treatment of such crude material to convert the oxidizable impurities to alkanesulfonyl chloride and thereafter hydrolyzing the alkanesulfonyl chloride to alkanesulfonic acid.

In the manufacture of alkanesulfonic acid by the reaction of an alkyl mercaptan or dialkyl disulfide with chlorine and aqueous hydrochloric acid at elevated temperature, a crude aqueous (20–35 wt. % water) alkanesulfonic acid containing oxidizable impurities is first formed. Dialkyl disulfide, alkyl alkane thiosulfonate and alkanesulfonyl chloride are the principal stable intermediates in this process. The total of dialkyl disulfide and alkyl alkane thiosulfonate is referred to as oxidizable impurities in the crude aqueous product. The crude product may be purified by heat stripping. Heat stripping, usually steam stripping, removes some of the oxidizable impurities overhead from the crude product but unexceptable levels remain and the bottoms product of the stripper must be further treated, e.g., by reaction with hydrogen peroxide or ozone, to reduce or eliminate the impurities.

THE PRIOR ART

The method of preparing aqueous alkanesulfonic acid by reacting an alkyl mercaptan or dialkyl disulfide with chlorine in the presence of aqueous hydrochloric acid at elevated temperature is known and shown, for example, in U.K. Patent Specification No. 1,350,328 published Apr. 18, 1974. This patent specification discloses steam stripping to purify the crude product.

BRIEF DESCRIPTION OF THE DRAWING

FIG. 1 of the drawing is a flow diagram of the preferred form of the process of the invention.

STATEMENT OF THE INVENTION

This invention is a process of preparing purified $C_1$–$C_8$ alkanesulfonic acid from crude aqueous $C_1$–$C_8$ alkanesulfonic acid containing oxidizable impurities, said process comprising treating said crude aqueous alkanesulfonic acid with chlorine in an amount effective to convert oxidizable impurities to the corresponding alkanesulfonyl chloride, and hydrolyzing said alkanesulfonyl chloride to alkanesulfonic acid.

DETAILED DESCRIPTION OF THE INVENTION

This invention relates to the use of chlorine to convert the oxidizable impurities in crude aqueous $C_1$–$C_8$ alkanesulfonic acid to alkanesulfonyl chloride and thereafter hydrolyzing the alkanesulfonyl chloride to alkanesulfonic acid thereby providing a purer alkanesulfonic acid product. The preparation of the crude aqueous alkanesulfonic acid is usually through the reaction of a $C_1$–$C_8$ alkyl mercaptan or $C_1$–$C_8$ alkyl disulfide and chlorine in the presence of aqueous hydrochloric acid at elevated temperature. While the process is applicable to $C_1$–$C_8$ alkanesulfonic acid including for example methane, ethane, propane, butane, propane, hexane, heptane and octanesulfonic acid, it is preferably used in the purification of crude aqueous $C_1$–$C_3$ alkanesulfonic acid and most preferably crude aqueous methanesulfonic acid (MSA) and, hereinafter, the purification of crude aqueous MSA will be used to demonstrate the invention.

In its most preferred form, the purification process of this invention is used for the treatment of crude aqueous MSA (20–35 weight % $H_2O$) prepared by the reaction of methyl mercaptan with chlorine in the presence of aqueous hydrochloric acid at an elevated temperature ranging from about 85° to 115° C., more preferably about 95° to 105° C. and typically about 98° C. The crude aqueous MSA recovered from this process contains appreciable quantities of stable intermediates including dimethyl disulfide (DMDS), methyl methane thiosulfonate (MMTS) and methanesulfonyl chloride (MSC). The total of the DMDS and MMTS is referred to as oxidizable impurities in the product specifications. After initial purification by steam stripping with superheated steam the bottoms discharge, prior to use of this invention, was observed to contain an average of 156 parts per million (ppm) of oxidizable impurities. If, in the past, it was found necessary to meet more stringent specifications regarding oxidizable impurities, the impurities were reacted with hydrogen peroxide or ozone by post-treating the aqueous MSA product with these agents.

In accordance with this invention, crude aqueous MSA containing oxidizable impurities is treated with chlorine in an amount sufficient to convert said oxidizable impurities to MSC and the MSC containing aqueous MSA is subjected to sufficient heat to hydrolyze the MSC to MSA. The amount of chlorine used will depend on whether the crude MSA is treated with chlorine as a part of a batch process or as a part of a continuous process. In the batch process, the crude aqueous MSA is preferably saturated with chlorine while in the continuous process for making and purifying aqueous MSA, small quantities (preferably 0.1% to 0.8% based on the weight of crude aqueous MSA) are injected into the discharge piping of a reactor producing, e.g., from 1000–1500 pounds per hour of crude aqueous MSA. In the continuous process, the chlorine is preferably sparged into the discharge tubing close to the bottom of the reactor to ensure that any unreacted chlorine will flow into the reactor to be used in the formation of the crude aqueous MSA from mercaptan.

Injection of chlorine into the bottom of the reactor for the production of crude aqueous MSA is not believed to be practical to meet the objective of this process since chlorine will form large bubbles in the reactor interior which cannot readily contact the oxidizable impurities of the crude aqueous MSA exiting the reactor bottom.

After leaving the production reactor, the crude aqueous MSA is conventionally passed to a steam stripper or the like to remove undesirable contaminates from the crude aqueous MSA. Chlorides, DMDS, MMTS, MSC, MSA, water and non-condensed chlorine are removed overhead, and an aqueous MSA with substantially reduced oxidizable impurities is recovered as a bottoms product. In accordance with this invention, MSC, which is produced by the conversion of oxidizable impurities with chlorine, is hydrolyzed in the steam stripper to MSA.

As an alternative to hydrolysis of the MSC in a steam stripper, a finishing reactor which subjects the MSC in the crude aqueous MSA to sufficient heat for a sufficient time to convert the MSC to MSA, may be employed. The product of the finishing reactor may then be subjected to steam stripping, if desired.

While the chlorination of the crude aqueous MSA is preferably carried out in the discharge line or piping, as close as possible to the reactor, beneficial purification results may be obtained by sparging chlorine into the crude at any point in the process subsequent to discharge from the reactor so long as the chlorine makes adequate contact with the oxidizable impurities to react therewith to form MSC and the MSC can be hydrolyzed to MSA. Line 22 in FIG. 1 of the drawing shows an alternative point of injection of chlorine into the aqueous MSA. If desired, the purified aqueous MSA is further treated to remove substantially all water, for example, by the evaporation procedures of U.S. Pat. Nos. 4,450,047 or 4,938,846.

The following examples demonstrate the process of this invention.

EXAMPLE 1

Aqueous methanesulfonic acid (30 wt. % $H_2O$) samples containing several hundred ppm of oxidizable impurities were chlorinated in batch operations by saturating the test samples with chlorine and allowing the chlorine to react with the impurities in the sample for from 48 to 72 hours. The aqueous MSA was then air stripped to remove excess chlorine. The batch chlorination reduced the oxidizable impurity content of the MSA samples to zero.

EXAMPLE 2

In a continuous operation, as shown in FIG. 1 of the Drawing, reactor 2 with sidearms used for reactant recycling and temperature control was operated at atmospheric pressure and a temperature of 98° C. to react methyl mercaptan entering the reactor at the rate of 475 pounds per hour through line 4 and chlorine entering the reactor at the rate of 2100 pounds per hour through line 6. Crude aqueous MSA (at a concentration of 70 weight 10 percent MSA) was discharged at the bottom of reactor 2 through line 12 at the rate of about 2.2 GPM (gallons/minute) while hydrogen chloride vapors were vented at the top of reactor 2 through line 8.

The crude aqueous MSA discharged through line 12 contained an average amount of oxidizable impurities in excess of 156 ppm. To help purify the crude aqueous MSA, chlorine was sparged into the crude through line 10 positioned close to the bottom of reactor 2 at a rate of about 20 standard cubic feet per minute (0.26% based on the weight of the crude aqueous MSA). Thereafter, the chlorine treated crude was pumped to the top of steam stripper 14 which was operated at a top temperature 118°–125° C. by injecting super-heated steam (227° C.) near the bottom through line 16. Volatiles were removed through line 18 at the top of the stripper 14 while the purified 70% aqueous MSA containing about 7 ppm of oxidizable impurities was recovered at the bottom through line 20 at a rate of from 1190 to 1370 pounds per hour.

When compared with the prior method of producing aqueous MSA wherein an average of 156 ppm of oxidizable impurities were found in the 70% aqueous MSA product discharged from the steam stripper treated under the same conditions, this secondary chlorination of the crude aqueous MSA product produced an unexpected improvement in this art. The products of the prior method, to obtain low oxidizable impurity content, had to be further treated with hydrogen peroxide in a time consuming operation using high cost equipment. The present process of simply sparging the crude with a small amount of chlorine, which may be diverted from the main chlorine stream to the reactor, is an inexpensive and readily adaptable modification of the known purification process.

We claim:

1. A process of preparing purified $C_1$–$C_8$ alkanesulfonic acid from crude aqueous $C_1$–$C_8$ alkanesulfonic acid containing oxidizable impurities, said process comprising treating said crude aqueous alkanesulfonic acid with chlorine in an amount effective to convert oxidizable impurities to the corresponding alkanesulfonyl chloride, and hydrolyzing said alkanesulfonyl chloride to alkanesulfonic acid.

2. The process of claim 1 wherein said alkanesulfonic acid is methanesulfonic acid.

3. A process of purifying crude aqueous $C_1$–$C_8$ alkanesulfonic acid containing oxidizable impurities prepared by the reaction of a $C_1$–$C_8$ alkyl mercaptan or $C_1$–$C_8$ alkyl disulfide and chlorine in the presence of aqueous hydrochloric acid at elevated temperature which process comprises treating said crude aqueous alkanesulfonic acid with chlorine in an amount effective to convert oxidizable impurities to the corresponding alkanesulfonyl chloride, and hydrolyzing said alkanesulfonyl chloride to alkanesulfonic acid.

4. The process of claim 3 wherein said crude aqueous $C_1$–$C_8$ alkanesulfonic acid is treated with chlorine diverted from the chlorine supply used to prepare said crude aqueous $C_1$–$C_8$ alkanesulfonic acid.

5. The process of claim 3 wherein said crude aqueous $C_1$–$C_8$ alkanesulfonic acid is stripped of impurities by contact with superheated steam subsequent to the chlorine treatment of said crude aqueous alkanesulfonic acid.

6. The process of claim 5 wherein said crude aqueous alkanesulfonic acid is a $C_1$–$C_4$ alkanesulfonic acid.

7. The process of claim 6 wherein said $C_1$–$C_4$ alkanesulfonic acid is methanesulfonic acid.

8. The process of claim 7 wherein the purified aqueous methanesulfonic acid is further treated to remove water.

9. A process of preparing $C_1$–$C_8$ alkanesulfonic acid from crude aqueous $C_1$–$C_8$ alkanesulfonic acid containing oxidizable impurities, said process comprising treating said crude aqueous alkanesulfonic acid with chlorine in an amount of from 0.1 to 0.8 percent based on the weight of the crude aqueous alkanesulfonic acid, and thereafter heat treating said aqueous sulfonic acid to a temperature ranging from about 97° to about 140° C. for at least about 300 seconds.

10. The process of claim 9 wherein said crude aqueous alkanesulfonic acid is a $C_1$–$C_4$ alkanesulfonic acid.

11. The process of claim 10 wherein said alkanesulfonic acid is methanesulfonic acid.

12. The process of claim 10 wherein the heat treated product is further treated to evaporate substantially all water therefrom.

* * * * *